US010429268B2

(12) United States Patent
Gao

(10) Patent No.: US 10,429,268 B2
(45) Date of Patent: Oct. 1, 2019

(54) LEAKAGE MONITORING SYSTEM FOR GEOMEMBRANES

(71) Applicant: Kang Gao, Guangdong (CN)

(72) Inventor: Kang Gao, Guangdong (CN)

( * ) Notice: Subject to any disclaimer, the term of this patent is extended or adjusted under 35 U.S.C. 154(b) by 0 days.

(21) Appl. No.: 15/972,181

(22) Filed: May 6, 2018

(65) Prior Publication Data

US 2019/0056287 A1 Feb. 21, 2019

(30) Foreign Application Priority Data

Aug. 18, 2017 (CN) .......................... 2017 1 0713260

(51) Int. Cl.
*B09C 1/00* (2006.01)
*G01M 3/40* (2006.01)
*G01N 27/20* (2006.01)
*G01M 3/18* (2006.01)
(Continued)

(52) U.S. Cl.
CPC ............... *G01M 3/40* (2013.01); *B09B 1/004* (2013.01); *E02D 31/006* (2013.01); *G01M 3/18* (2013.01); *G01N 27/205* (2013.01); *B09B 1/00* (2013.01)

(58) Field of Classification Search
CPC ......... B09B 1/00; B09B 1/004; E02D 31/004; E02D 31/006; E02D 31/008; E02D 31/025
See application file for complete search history.

(56) References Cited

U.S. PATENT DOCUMENTS 5,076,728 A * 12/1991 Golding .................... B09B 1/00
405/129.5
5,980,155 A * 11/1999 Jones ........................ B32B 5/26
405/43
(Continued)

FOREIGN PATENT DOCUMENTS

WO WO-9412736 A1 * 6/1994 ........... E02D 31/004

OTHER PUBLICATIONS

Randin J.P. (1981) Nonmetallic Electrode Materials. In: Bockris J.O., Conway B.E., Yeager E., White R.E. (eds) Electrochemical Materials Science. Comprehensive Treatise of Electrochemistry, vol. 4. Springer, Boston, MA (Year: 1981).*

*Primary Examiner* — Frederick L Lagman
(74) *Attorney, Agent, or Firm* — Global IP Services; Tianhua Gu

(57) ABSTRACT

A leakage monitoring system for geomembranes comprises a power supply unit having two supply electrodes made from a nonmetallic conductive material and respectively connected to a membrane top and a membrane bottom of a primary geomembrane; a plurality of monitoring sensor electrodes made from the nonmetallic conductive material, uniformly arranged below the primary geomembrane and used for acquiring potentials at corresponding positions below the primary geomembrane; a data acquisition unit used for acquiring potential data of each monitoring sensing electrode; and a control and analysis unit used for analyzing the potential data of each monitoring sensor electrode acquired by the data acquisition unit, determining an abnormal potential area below the primary geomembrane to determine a leakage position of the primary geomembrane and giving an alarm. The abnormal potential area below the geomembrane can be determined to determine the specific leakage position of the geomembrane and give the alarm.

10 Claims, 1 Drawing Sheet

(51) Int. Cl.
*E02D 31/00* (2006.01)
*B09B 1/00* (2006.01)

(56) References Cited

U.S. PATENT DOCUMENTS

| | | | | |
|---|---|---|---|---|
| 6,016,714 | A * | 1/2000 | Smith | B09B 1/00 588/260 |
| 6,056,477 | A * | 5/2000 | Ueda | B09B 1/00 340/605 |
| 6,331,778 | B1 * | 12/2001 | Daily | G01M 3/16 324/512 |
| 6,648,552 | B1 * | 11/2003 | Smith | B09B 1/00 405/129.5 |
| 8,566,051 | B2 * | 10/2013 | Gunness | E04D 13/006 324/444 |
| 9,033,620 | B2 * | 5/2015 | Youngblood, Jr. | G01M 3/40 405/302.7 |
| 2002/0028110 | A1 * | 3/2002 | Rhee | G01M 3/04 405/129.5 |
| 2006/0105163 | A1 * | 5/2006 | Bray | B32B 27/06 428/339 |
| 2011/0178747 | A1 * | 7/2011 | Gunness | G01M 3/16 702/65 |
| 2017/0138812 | A1 * | 5/2017 | Nosko | G01M 3/16 |

* cited by examiner

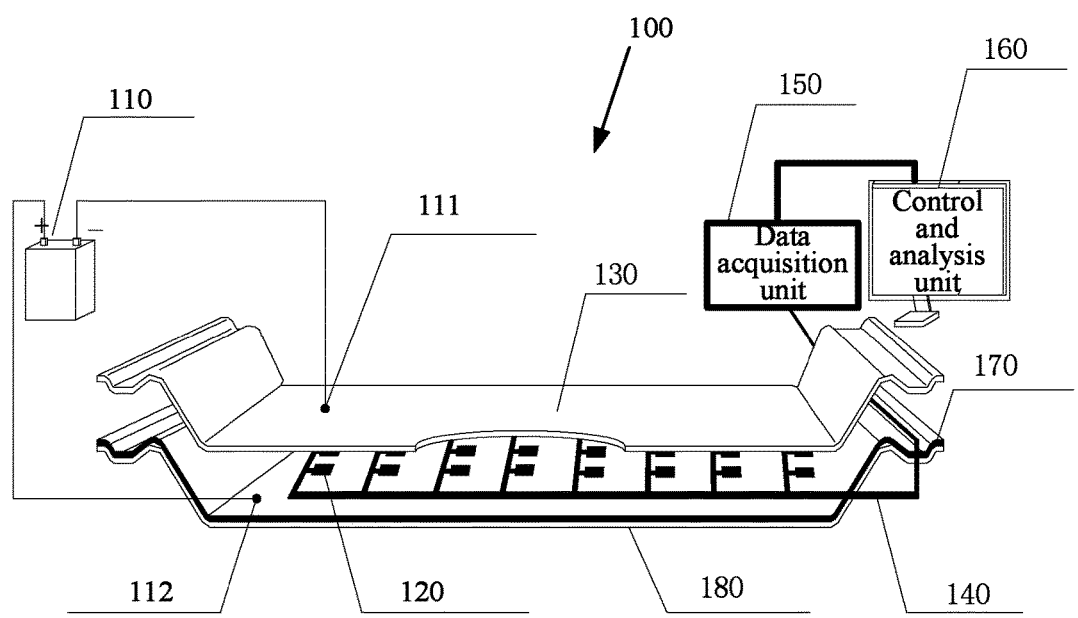

LEAKAGE MONITORING SYSTEM FOR GEOMEMBRANES

BACKGROUND OF THE PRESENT INVENTION

Field of Invention

The present invention relates to the technical field of geomembrane leakage-proof engineering, in particular to the technical field of long-term leakage monitoring in geomembrane containment engineering, specifically leakage monitoring system for geomembranes.

COPYRIGHT DECLARATION

The content disclosed by the present disclosure document contains materials protected by the copyright. The copyright belongs to the copyrighter. The copyrighter does not object to anybody copying the patent document or the patent disclosure existing in official records and files of the Patent & Trademark Office.

Description of Related Arts

Projects such as landfills, artificial lakes, reservoirs, mine tailing ponds and heap leaching fields generally adopt containment geomembranes to construct leakage-proof systems. However, the geomembranes are possibly damaged and destructed at manufacturing, transportation, construction and installation etc., and the damaged geomembranes inevitably cause leakage. In case of pollution caused by landfills, leaking leachate inevitably pollutes surrounding environments such as underground water and causes environmental damage. A traditional landfill leakage monitoring method is to adopt a monitoring well, this monitoring method is comparatively lagging, it can be found only after the environment has been polluted to some extent, leakage has already occurred for a period of time and diffused to the underground water. For a metallurgical heap leaching field project, solution leakage is equivalent to profit loss.

The traditional monitoring well method can only determine that landfill geomembranes are damaged and leakage occurs, but cannot position the holes.

SUMMARY OF THE PRESENT INVENTION

In view of the above-mentioned disadvantages of the prior art, the purpose of the embodiment according to the present invention is to provide a leakage monitoring system for geomembranes, which is used for solving the problem that leakage cannot be positioned when a geomembrane containment system damaged and leaks in construction and operation processes in the prior art.

In order to achieve the above-mentioned purpose and other purposes, the embodiment of the present invention provides a leakage monitoring system for geomembranes, comprising: a power supply unit having two supply electrodes made from a nonmetallic conductive material and respectively connected to a membrane top and a membrane bottom of a primary geomembrane such that the membrane top and the membrane bottom of the primary geomembrane respectively form electric fields; a plurality of monitoring sensor electrodes uniformly arranged below the primary geomembrane and used for acquiring potentials at corresponding positions below the primary geomembrane, wherein the monitoring sensor electrodes are made from the nonmetallic conductive material; a data acquisition unit connected with each monitoring sensor electrode through a signal transmission cable and used for acquiring potential data of each monitoring electrode; and a control and analysis unit connected with the data acquisition unit and used for analyzing the potential data of each monitoring sensor electrode acquired by the data acquisition unit, determining an abnormal potential area between the monitoring sensor electrodes below the primary geomembrane to determine a leakage position of the primary geomembrane and giving an alarm.

In one embodiment of the present invention, the nonmetallic conductive material is formed by mixture of one of graphene, carbon nanotube, conductive carbon black, conductive carbon fiber, metal powder or a combination thereof, and a nonmetallic high-molecular polymer.

In one embodiment of the present invention, the electrical resistivity of the monitoring sensor electrodes is smaller than $10^{-5}$ $\Omega \cdot m$.

In one embodiment of the present invention, the leakage monitoring system for geomembranes further comprises a secondary geomembrane; the two supply electrodes of the power supply unit are respectively connected to the membrane top and the membrane bottom of the primary geomembrane; and the monitoring sensor electrodes are located below the primary geomembrane.

In one embodiment of the present invention, the monitoring sensor electrodes are arranged on a conductive geotextile or a conductive geotechnical geocomposite in equal distance; the distance is within 0.5~20 m; and an arrangement point position of each monitoring sensor electrode is determined and recorded through a GPS high accuracy position system.

In one embodiment of the present invention, the conductive geocomposite comprises a geonet and a nonmetallic conductive geotextile bonded to one surface or two surfaces of the drainage geonet.

In one embodiment of the present invention, the power supply unit adopts a high-voltage direct-current power source or positive and negative pulse square waves supply power.

In one embodiment of the present invention, the monitoring sensor electrodes and wire cables in the signal transmission cable are connected and then sealed, wherein the material of outer insulating layers of the wire cables in the signal transmission cable is the same as the material of the nonmetallic high density polymer in the monitoring sensor electrodes.

In one embodiment of the present invention, the data acquisition unit adopts PXI architecture, PXIE architecture, PCI architecture, PCIE architecture or LXI architecture; and the data acquisition unit comprises a data acquisition card or a Digital Multimeters (DMMs) connected with each monitoring sensor electrode; or the data acquisition unit comprises a data acquisition card or a Digital Multimeters (DMMs) and a matrix switch or a multiplexer relay module connected between each monitoring sensor electrode and the data acquisition card or Digital Multimeters (DMMs).

In one embodiment of the present invention, the control and analysis unit acquire a 2D or 3D potential map according to the potential data of each monitoring sensor electrode and determines the abnormal potential area between the monitoring sensor electrodes below the primary geomembrane according to the potential map to determine the leakage position of the primary geomembrane.

As described above, the leakage monitoring system for geomembranes provided by the present invention has the following beneficial effects:

In the present invention, by arranging the monitoring sensor electrodes made from the nonmetallic conductive material below the geomembrane, the problem that metallic electrodes cannot resist acid and alkali and resist electrochemical corrosion when the metallic electrodes are used and the potential risk that the geomembrane is damaged when metallic electrodes are used can be avoided; and by acquiring the potential data acquired by each monitoring sensor electrode, the abnormal potential area below the geomembrane can be determined to determine the specific leakage position of the geomembrane and give the alarm prompt, and the problem that the leakage cannot be positioned when the geomembrane leakage-proof system is damaged and leaks in construction and operation processes in the prior art is effectively solved.

BRIEF DESCRIPTION OF THE DRAWINGS

In order to more clearly describe the technical solution in the embodiment of the present invention, the drawings which need to be used in the description of the embodiments will be briefly described below. Obviously, the drawings described below are just some embodiments of the present invention. One skilled in the art may further obtain other drawings according to these drawings without contributing any inventive labor.

FIG. 1 illustrates a structural schematic diagram of a leakage monitoring system for geomembranes in one embodiment of the present invention.

DESCRIPTION OF COMPONENT MARK NUMBERS

100 Leakage monitoring system
110 Power supply unit
111 Supply electrode above the membrane
112 Supply electrode below the membrane
120 Monitoring sensor electrode
130 Primary geomembrane
140 Signal transmission cable
150 Data acquisition unit
160 Control and analysis unit
170 Conductive geocomposite or Geotextile
180 Secondary geomembrane

DETAILED DESCRIPTION OF THE PREFERRED EMBODIMENTS

The implementation modes of the present invention will be described below through specific embodiments. One skilled in the art may easily understand other advantages and effects of the present invention according to the content disclosed by the description.

Please refer to FIG. 1. It shall be understood that the structures, scales, sizes and the like illustrated in the attached drawing of the description are only used for cooperating with the contents disclosed by the description to allow one skilled in the art to understand and read instead of limiting the implementable limitation conditions of the present invention, and thus have no technical substantive meanings; and any structural modifications, changes of scaling relations or adjustments to sizes shall still fall into the scope which can be covered by the technical contents disclosed by the present invention under the situation that the effects which can be produced by the present invention and the purposes which can be achieved by the present invention are not influenced. In addition, words such as "above", "below", "left", "right", "middle" and "one" cited in the description are just used for facilitating clear description instead of limiting the implementable scope of the present invention. Changes or adjustments of relative relations thereof shall also be deemed as the implementable scope of the present invention under the situation that the technical contents are not substantively changed.

The purpose of the embodiment of the present invention is to provide a leakage monitoring system for geomembranes, which is used for solving the problem that leakage position cannot be positioned when a geomembrane containment system is damaged and leaks in construction and operation processes in the prior art. The principle and implementation modes of the leakage monitoring system for geomembranes provided by the present invention will be described below in detail such that one skilled in the art can understand the leakage monitoring system for geomembranes provided by the present invention without contributing any inventive labor.

The embodiment of the present invention provides a leakage monitoring system for geomembranes, which is used for monitoring the damage and leakage situations of geomembranes during operation. Specifically, as illustrated in FIG. 1, the leakage monitoring system 100 comprises a power supply unit 110, a plurality of monitoring sensor electrodes 120, a data acquisition unit 150 and a control and analysis unit 160.

In this embodiment, the power supply unit 110 provides potentials of a membrane top and a membrane bottom of a primary geomembrane 130, the power supply unit 110 has two supply electrodes made of a nonmetallic conductive material, i.e., a supply electrode 111 above the membrane (which is a negative electrode, for example) and a supply electrode 112 below the membrane (which is a positive electrode, for example), and the supply electrode 111 above the membrane and the supply electrode 112 below the membrane are respectively connected to a membrane top and a membrane bottom of the primary geomembrane 130 such that the membrane top and the membrane bottom of the primary geomembrane 130 respectively form electric fields.

Herein, the supply electrodes of the power supply unit 110 are made of a nonmetallic conductive material to form nonmetallic supply electrodes, so as to avoid that metallic electrodes will be corroded and oxidized when used. In this embodiment, the nonmetallic conductive material is formed by but not limited to mixture of one of conductive carbon black, graphene, carbon nanotube, conductive carbon fiber, metal powder or a combination thereof, and a nonmetallic high-molecular polymer. The nonmetallic high-molecular polymer can be, for example, polyethylene, polypropylene, nylon, polyoxymethylene (POM) and polytetrafluoroethylene etc., and the nonmetallic high-molecular polymer is preferably formed by mixture of acid-resistant and alkali-resistant plastic materials such as high-density polyethylene.

The resistivity of the nonmetallic supply electrodes is required to reach a conduction level, which equivalently the resistivity is smaller than $10^{-5}$ Ω·m.

The power supply source of the power supply unit 110 is connected with the nonmetallic supply electrodes by adopting metallic wires, and the nonmetallic supply electrodes and the metallic wires are connected by means of full sealing to prevent the metallic wires from exposing, which results in being corroded and damaged.

In this embodiment, the power supply unit 110 is subject to special transformation and waveform treatment and adopts a high-voltage direct-current power source or positive and negative pulse square waves to supply power, i.e., the power supply unit 110 may adopt a high-voltage direct-current power source to supply power, or may also adopt positive and negative pulse square waves to supply power.

In this embodiment, the monitoring sensor electrodes 120 acquire potentials of positions in certain distance below the primary geomembrane 130, and the plurality of monitoring sensor electrodes 120 are uniformly arranged below the primary geomembrane 130 and acquire potential at corresponding positions below the primary geomembrane 130. Specifically, in this embodiment, the monitoring sensor electrodes 120 are arranged below the primary geomembrane 130 by means of dot matrix arrangement. Herein, the monitoring sensor electrodes 120 are arranged according to equal distance, and the distance is 0.5~20 m, generally does not exceed 10 m and conventionally is 5~8 m.

Once leakage occurs in the primary geomembrane 130, liquid on the primary geomembrane 130 leaks through the membrane, the monitoring sensor electrodes 120 below the primary geomembrane 130 can detect potential change caused by leakage, and by acquiring the potential of each monitoring sensor electrode 120 and analyzing the data, a potential map is drawn and thus leakage positions can be determined.

In this embodiment, the shape of the monitoring sensor electrodes 120 is not limited, and which may be a cylinder shape, a cuboid shape, a cube shape or the like.

Herein, the monitoring sensor electrodes 120 are made from the nonmetallic conductive material. In this embodiment, the nonmetallic conductive material is formed by but not limited to mixture of a nonmetallic high-molecular polymer and one of conductive carbon black, graphene, carbon nanotube, conductive carbon fiber, metal powder or a combination thereof. For example, polyethylene, polypropylene, nylon, polyoxymethylene (POM) and polytetrafluoroethylene may be selected, and the nonmetallic high-molecular polymer is preferably formed by mixture of acid-resistant and alkali-resistant plastic materials.

In this embodiment, the leakage-proof geomembrane may be a single-layer membrane and may also be a dual-layer membrane, comprising a primary geomembrane 130 and a secondary geomembrane 180.

Thus, in this embodiment, the leakage monitoring system 100 may be used for monitoring leakage of a single-layer geomembrane, in this case, a clay layer or GCL is generally below the primary geomembrane 130, and in an area in which the soil property of the clay layer is not good or GCL is too dry, a layer of conductive geocomposite or conductive geotextile needs to be added as a conductive layer for leakage monitoring system.

In this embodiment, the leakage monitoring system 100 may also be used for monitoring leakage of a dual-layer geomembrane; and when the geomembrane 1 comprises a primary geomembrane 130 and a second leakage-proof geomembrane 180, the two supply electrodes of the power supply unit 110 are respectively connected to a membrane top and a membrane bottom of the primary geomembrane, and the monitoring sensor electrodes 120 are located below the primary geomembrane.

In this embodiment, when the geomembrane comprises a primary geomembrane 130 and a second geomembrane 180, the monitoring sensor electrodes 120 are preferably arranged on a conductive geotextile or conductive geocomposite 170. Herein, the monitoring sensor electrodes 120 are arranged on the conductive geotextile or conductive geocomposite 170 or other materials having a conductive function in equal distance. The selected distance is within 0.5~20 m, generally does not exceed 10 m and conventionally is 5~8 m. An arrangement point position of each monitoring sensor electrode is determined through a GPS high accuracy position system, such that it can be rapidly positioned during maintenance and repair.

In this embodiment, the conductive geocomposite 170 comprises a geonet and a nonmetallic conductive geotextile bonded to one surface or two surfaces of the geonet. When the leakage monitoring system 100 for the primary geomembrane 130 is adhered to one surface of the geonet, a metallic conductive geotextile or nonconductive geotextile is adhered to the other surface of the geonet. A conductive geocomposite made manufacturing by compositing nonconductive nonwoven fabrics on both surfaces of a geonet having a conductive function may also be adopted.

Herein, the nonmetallic conductive geotextile comprises a geotextile and a nonmetallic conductive structure connected with the geotextile, and the geotextile is enabled to have a conductive function through the nonmetallic conductive structure. In this embodiment, the conductive material for the geotextile is a nonmetallic material, and the geotextile made in this way has functions such as aging resistance, corrosion resistance, acid and alkali resistance and electrochemical corrosion resistance, and can adapt to severe environments. Specifically, in this embodiment, the nonmetallic conductive structure comprises one of carbon nanotube, graphene, superconductive carbon black or a combination thereof.

Herein, one specific structure of the nonmetallic conductive structure is continuous conductive coating formed by mixture of one of the carbon nanotube, the graphene, the superconductive carbon black or a combination thereof, and a binder, and the conductive coating is coated onto the surface of the geotextile. The conductive coating is coated onto one surface or two surfaces of the geotextile.

Another specific structure of the nonmetallic conductive structure is a conductive fiber made from one of the carbon nanotube, the graphene, the superconductive carbon black, plastic particles or a combination thereof; and the conductive fiber is a nonmetallic conductive fiber. When the geotextile is made, the conductive fiber is added, such that the conductive fiber is connected into the geotextile to form a nonmetallic conductive blended geotextile.

In this embodiment, in order to make the resistivity of the monitoring sensor electrodes 120 reach the conductor requirement, the resistivity of the monitoring sensor electrodes 120 is smaller than $10^{-5}$ Ω·m.

In this embodiment, the data acquisition unit 150 is connected with each monitoring sensor electrode 120 through a signal transmission cable 140 to acquire potential data of each monitoring sensing electrode 120.

In this embodiment, conductors in the signal transmission cable 140 are made stainless steel wires and copper wires, and the monitoring sensor electrodes 120 and wire cables in the signal transmission cable 140 are sealing connected by means such as welding or bonding, and then are sealed, wherein the material of outer insulating layers of the wire cables in the signal transmission cable 140 is the same as the material of the nonmetallic high-molecular polymer in the monitoring sensor electrodes 120, and especially HDPE (High Density Polyethylene) is selected for manufacturing. The outer insulating layers of the wire cables are connected with the monitoring sensor electrodes 120 by means of hot melting or high-frequency ultrasonic welding. However, the connection manners are not limited to the above-mentioned connection manners, which may also be adhesive connection injection molding.

In this embodiment, the data acquisition unit adopts PXI (PCI extensions for Instrumentation) architecture, PXIE architecture, PCI (Peripheral Component Interconnect) architecture, PCIE architecture or LXI (LAN extension for instrumentation) architecture. PXIE is an up grading of PXI and represents PXI Express, and PCIE is an upgrading of PCI and represents PCI Express. The data acquisition unit 150 comprises a data acquisition card or a digital multimeter connected with each monitoring sensor electrode 120; or the data acquisition unit 150 comprises a data acquisition card or a digital multimeter, and a matrix switch or a multiplexer connected between each monitoring sensor electrode 120 and the data acquisition card or digital multimeter.

Each monitoring sensor electrode 120 may be directly connected with the data acquisition card through the signal transmission cable 140. In the situation that there are more acquisition points, the number of the monitoring sensor electrodes 120 is larger, which is generally greater than 48, the matrix switch or the multiplexer is adopted for connecting each monitoring sensor 120 through the signal transmission cable 140, and then the matrix switch and the multiplexer is connected to the data acquisition card or the digital multimeter.

In this embodiment, the control and analysis unit 160 is connected with the data acquisition unit 150 and is used for analyzing the potential data of each monitoring sensor electrode 120 acquired by the data acquisition unit 150, determining an abnormal potential area between the monitoring sensor electrodes 120 below the primary geomembrane 130 thereby to determine a leakage position of the primary geomembrane 130 and give an alarm. According to the coordinate position of the alarm point, the actual damage position is found out through GPS positioning.

Herein, when the power supply unit 110 adopts positive and negative pulse square waves to supply power, a numerical value obtained by subtracting potential data measured in a negative pulse square wave power supply mode from potential data measured in a positive pulse square wave power supply mode is used as a numerical value for final analysis. When the power supply unit 110 adopts high-voltage direct-current power source to supply power, the measured data are directly adopted for analysis.

Besides, the power supply unit 110 may adopt a zoned power supply mode and the coverage range of each supply electrode is obtained according to a field test.

Specifically, the control and analysis unit 160 acquires a 2D or 3D potential map according to the potential data of each monitoring sensor electrode 120 and determines the abnormal potential area between the monitoring sensor electrodes 120 below the primary geomembrane 130 according to the potential map to determine the leakage position of the primary geomembrane 130. Through long-term monitoring, the damage and leakage situations of the primary geomembrane 130 can be monitored in real time or at different periods of time, and after the damage is repaired, the pollutant is prevented from leaking and causing environmental pollution. For a metallurgical heap leaching field, solution containing minerals can be prevented from leaking and causing economic losses and environmental pollution. Through the leakage monitoring system 100 provided by this embodiment, zero leakage of the structure of the primary geomembrane 130 can be realized.

In order to enable one skilled in the art to further understand the principle of the present invention, the monitoring process of this embodiment will be described below, specifically as follows:

The supply electrodes of the power supply unit 110 are connected with the power supply source, the supply electrode 111 above the membrane and the supply electrode 112 below the membrane are respectively connected with the top and the bottom of the primary geomembrane 130 such that the top and the bottom of the primary geomembrane 130 respectively form electric fields to establish a stable potential field, and once the primary geomembrane 130 is damaged and leaks, the loophole area forms a point power supply potential, and potential at this point will mutate, the monitoring sensor electrode 120 transmits the acquired potential to the matrix card and the data acquisition card of the data acquisition unit 150 through the signal transmission cable 140, the acquired potential data enter the control and analysis unit 160, the control and analysis unit 160 performs statistical analysis to the acquired potential data, a 2D or 3D potential map is drawn by utilizing drawing software, the damage and leakage portion of the primary geomembrane 130 is determined according to the potential map and an alarm can be given.

Thus, the leakage monitoring system 100 in this embodiment adopts an electrical long-term leakage detection system to perform real-time monitoring, can find leakage in time and can position the holes when leakage occurs, i.e., when an alarm is given. When the leakage monitoring system 100 is constructed, the monitoring sensor electrodes 120 for positioning are installed below the primary geomembrane 130, the monitored electrical signals are transmitted to the data acquisition unit 150 and the control and analysis unit 160 (central processing computer) through the cable to analyze the data in real time, such that the safety operation situation of the primary geomembrane 130 of the landfill is obtained. The completeness of the containment structure is monitored in long and real time to find leakage in time, an alarm can be given at the early stage of leakage, the position of the loophole can be determined, proper engineering measures are taken to repair the primary geomembrane 130 at the leakage and damage position, the completeness of the primary geomembrane 130 at the entire operation period is guaranteed and zero leakage is realized. For a pollutant place, leaking liquid can be prevented from polluting the surrounding environment; and for a mine heap leaching field, leakage can be prevented from causing economic losses.

To sum up, in the present invention, by arranging the monitoring sensor electrodes 120 made from the nonmetallic conductive material below the geomembrane, the problem that metallic electrodes cannot resist acid and alkali and resist electrochemical corrosion when the metallic electrodes are used and the potential risk that the geomembrane is damaged when metallic electrodes are used can be avoided; and by acquiring the potential data acquired by each monitoring sensor electrode 120, the abnormal potential area below the geomembrane can be determined to determine the specific leakage position of the geomembrane and give the alarm prompt, and the problem that the leakage cannot be positioned when the geomembrane containment system is damaged and leaks in construction and operation processes in the prior art is effectively solved. Therefore, the present invention effectively overcomes various disadvantages in the prior art and thus has a very great industrial utilization value.

The above-mentioned embodiments are just used for exemplarily describing the principle and effect of the present invention instead of limiting the present invention. One skilled in the art may make modifications or changes to the above-mentioned embodiments without departing from the spirit and scope of the present invention. Therefore, all equivalent modifications or changes made by those who have common knowledge in the art without departing from the spirit and technical thought disclosed by the present invention shall be still covered by the claims of the present invention.

What is claimed is:

1. A leakage monitoring system for geomembranes comprising:
    a power supply unit having two supply electrodes made from a nonmetallic conductive material and respectively connected to a geomembrane top and a geomembrane bottom of a primary geomembrane such that the membrane top and the membrane bottom of the primary geomembrane respectively form electric fields;
    a plurality of monitoring sensor electrodes uniformly arranged below the primary geomembrane and used for acquiring potentials at corresponding positions below the primary geomembrane;
    wherein the monitoring sensor electrodes are made from the nonmetallic conductive material and are arranged on a conductive geotextile or a conductive geocomposite in equal distance, the distance is within 0.5~20 m; and an arrangement point position of each monitoring sensor electrode is determined and recorded through a GPS high accuracy position system;
    a data acquisition unit connected with each monitoring sensor electrode through a signal transmission cable and used for acquiring potential data of each monitoring sensing electrode; and
    a control and analysis unit connected with the data acquisition unit and used for analyzing the potential data of each monitoring sensor electrode acquired by the data acquisition unit, determining an abnormal potential area between the monitoring sensor electrodes below the primary geomembrane to determine a leakage position of the primary geomembrane and giving an alarm prompt.

2. The leakage monitoring system for geomembranes according to claim 1, characterized in that the nonmetallic conductive material is formed by mixture of one of conductive carbon black, graphene, carbon nanotube, conductive carbon fiber, metal powder or a combination thereof, and a nonmetallic high-density polymer.

3. The leakage monitoring system for geomembranes according to claim 2, characterized in that the monitoring sensor electrodes and wire cables in the signal transmission cable are connected and then sealed, wherein the material of outer insulating layers of the wire cables in the signal transmission cable is the same as the material of the nonmetallic high-molecular polymer in the monitoring sensor electrodes.

4. The leakage monitoring system for geomembranes according to claim 2, characterized in that the resistivity of the monitoring sensor electrodes is smaller than $10^{-5}$ Ω·m.

5. The leakage monitoring system for geomembranes according to claim 1, characterized in that the resistivity of the monitoring sensor electrodes is smaller than $10^{-5}$ Ω·m.

6. The leakage monitoring system for geomembranes according to claim 1, characterized in that the leakage monitoring system for geomembranes further comprises a secondary geomembrane; the two supply electrodes of the power supply unit are respectively connected to the membrane top and the membrane bottom of the primary geomembrane; and the monitoring sensor electrodes are located below the primary geomembrane.

7. The leakage monitoring system for geomembranes according to claim 1, characterized in that the conductive geocomposite comprises a geonet and a nonmetallic conductive geotextile adhered to one surface or two surfaces of the geonet.

8. The leakage monitoring system for geomembranes according to claim 1, characterized in that the power supply unit adopts a high-voltage direct-current power source or positive and negative pulse square waves to supply power.

9. The leakage monitoring system for geomembranes according to claim 1, characterized in that the data acquisition unit adopts PXI architecture, PXIE architecture, PCI architecture, PCIE architecture or LXI architecture; and the data acquisition unit comprises a data acquisition card or a digital multimeter connected with each monitoring sensor electrode; or the data acquisition unit comprises a data acquisition card or a digital multimeter and a matrix switch or a multiplexer connected between each monitoring sensor electrode and the data acquisition card or digital multimeter.

10. The leakage monitoring system for geomembranes according to claim 1, characterized in that the control and analysis unit acquires a 2D or 3D potential map according to the potential data of each monitoring sensor electrode and determines the abnormal potential area between the monitoring sensor electrodes below the primary geomembrane according to the potential map to determine the leakage position of the primary geomembrane.

* * * * *